(12) United States Patent
Tethrake et al.

(10) Patent No.: US 8,454,613 B2
(45) Date of Patent: Jun. 4, 2013

(54) METHOD AND APPARATUS FOR SURGICAL INSTRUMENT IDENTIFICATION

(75) Inventors: Steven Tethrake, Collierville, TN (US);
Paul Elliott, Collierville, TN (US);
Jeffrey Nycz, Warsaw, IN (US); Robert Varner, Germantown, TN (US); Mark Pelo, Macy, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 264 days.

(21) Appl. No.: 12/729,497

(22) Filed: Mar. 23, 2010

(65) Prior Publication Data

US 2010/0176925 A1 Jul. 15, 2010

Related U.S. Application Data

(63) Continuation of application No. 11/116,379, filed on Apr. 28, 2005, now Pat. No. 7,837,694.

(51) Int. Cl.
*A61F 2/46* (2006.01)

(52) U.S. Cl.
USPC ........................................ 606/86 R; 340/10.1

(58) Field of Classification Search
USPC ............... 606/86 R, 88, 130, 170, 79, 80, 82; 340/572.1, 572.8, 572.9
See application file for complete search history.

(56) References Cited

U.S. PATENT DOCUMENTS

| | | | |
|---|---|---|---|
| 4,075,632 A | 2/1978 | Baldwin et al. |
| 4,360,801 A | 11/1982 | Duhame |
| 4,390,880 A | 6/1983 | Henoch |
| 4,688,026 A | 8/1987 | Scribner et al. |
| 4,730,188 A | 3/1988 | Milheiser |
| 4,739,328 A | 4/1988 | Koelle et al. |
| 5,030,807 A | 7/1991 | Landt et al. |
| 5,378,880 A | 1/1995 | Eberhardt |
| 5,621,199 A | 4/1997 | Calari et al. |
| 5,923,001 A | 7/1999 | Morris et al. |
| 5,963,134 A | 10/1999 | Bowers et al. |

(Continued)

FOREIGN PATENT DOCUMENTS

| | | |
|---|---|---|
| DE | 19514284 A1 | 10/1996 |
| DE | 10014542 A1 | 10/2001 |
| WO | WO 2004042677 A | 5/2004 |

OTHER PUBLICATIONS

Presentation by Innovision Research and Technology, PLC at the "RFID in Healthcare" conference in Washington, DC. on Dec. 2 and 3, 2003.

(Continued)

*Primary Examiner* — Eduardo C Robert
*Assistant Examiner* — Tara Carter

(57) ABSTRACT

Systems and methods for identifying surgical instruments by use of radio-frequency identification tags (RFID) are disclosed. In the systems and methods, each of a plurality of surgical instruments is provided with at least one RFID transponder tag storing identification information associated with the corresponding instrument. The tag may be adhered to, embedded, or potted within a portion of the instrument. Using an RFID reading device, a user may interrogate the tag, thereby identifying the particular instrument. This identification information may be used to index a database and retrieve a data record unique to that instrument. The systems and methods allow a user to track, inspect, and verify inbound and outbound surgical instruments, to assess, for example, the surgical instruments' duty life cycle usage.

13 Claims, 10 Drawing Sheets

U.S. PATENT DOCUMENTS

| | | | |
|---|---|---|---|
| 6,158,437 A | 12/2000 | Vagley | |
| 6,164,738 A | 12/2000 | Dane et al. | |
| 6,172,609 B1 | 1/2001 | Lu et al. | |
| 6,265,976 B1 | 7/2001 | Roesner | |
| 6,318,636 B1 | 11/2001 | Reynolds et al. | |
| 6,405,863 B1 | 6/2002 | Dhindsa | |
| 6,415,978 B1 | 7/2002 | McAllister | |
| 6,426,041 B1 * | 7/2002 | Smith | 422/28 |
| 6,429,776 B1 | 8/2002 | Alicot et al. | |
| 6,476,708 B1 | 11/2002 | Johnson | |
| 6,480,101 B1 | 11/2002 | Kelly et al. | |
| 6,523,752 B2 | 2/2003 | Nishitani et al. | |
| 6,646,241 B1 | 11/2003 | Varma et al. | |
| 6,664,520 B2 | 12/2003 | Clothier | |
| 6,669,089 B2 | 12/2003 | Cybulski et al. | |
| 6,677,852 B1 | 1/2004 | Landt | |
| 6,701,508 B1 | 3/2004 | Bartz et al. | |
| 6,777,623 B2 | 8/2004 | Ballard | |
| 6,825,766 B2 | 11/2004 | Hewitt et al. | |
| 6,853,303 B2 | 2/2005 | Chen et al. | |
| 6,861,954 B2 | 3/2005 | Levin | |
| 6,866,147 B2 | 3/2005 | Barwick | |
| 2002/0032435 A1 | 3/2002 | Levin | |
| 2002/0063622 A1 | 5/2002 | Armstrong et al. | |
| 2002/0105424 A1 | 8/2002 | Alicot et al. | |
| 2002/0143320 A1 | 10/2002 | Levin | |
| 2002/0188259 A1 | 12/2002 | Hickle et al. | |
| 2003/0093103 A1 * | 5/2003 | Malackowski et al. | 606/170 |
| 2003/0164401 A1 | 9/2003 | Andreasson et al. | |
| 2003/0174099 A1 | 9/2003 | Bauer et al. | |
| 2003/0189094 A1 | 10/2003 | Trabitz | |
| 2003/0196837 A1 | 10/2003 | Ballard | |
| 2004/0008123 A1 | 1/2004 | Carrender et al. | |
| 2004/0022227 A1 | 2/2004 | Lynch et al. | |
| 2004/0031626 A1 | 2/2004 | Morris et al. | |
| 2004/0069851 A1 | 4/2004 | Grunes et al. | |
| 2004/0100384 A1 | 5/2004 | Chen et al. | |
| 2004/0160233 A1 | 8/2004 | Forster | |
| 2004/0174244 A1 | 9/2004 | Eidemiller | |
| 2004/0174261 A1 * | 9/2004 | Volpi et al. | 340/572.1 |
| 2004/0220602 A1 * | 11/2004 | Deng et al. | 606/170 |
| 2004/0220860 A1 | 11/2004 | Persky et al. | |
| 2004/0250819 A1 | 12/2004 | Blair et al. | |
| 2004/0267297 A1 | 12/2004 | Malackowski | |
| 2005/0003757 A1 | 1/2005 | Anderson | |
| 2005/0012617 A1 | 1/2005 | DiSilvestro et al. | |

OTHER PUBLICATIONS (http://rfidjournal.com/article/view/112) RFID Journal, Can RFID Cure Healthcare's Ills?, Nov. 12, 2002.

http://www.eetimes.com/showPressRelease.jhtml?articleID=57907) EE Times www,eetimes.com) "T-Ink™ Unique Conductive Ink Technology to Be Featured" Feb. 14, 2003, pp. 1-2.

http://americanprinter.com/microsites/magazinearticle.asp?mode=print&magazinearticleid . . . ) American Printer (www.americanprinter.com) "Tracking RFID Progress" Jan. 1, 2004, pp. 1-3.

* cited by examiner

METHOD AND APPARATUS FOR SURGICAL INSTRUMENT IDENTIFICATION

CROSS-REFERENCE

This application is a continuation of U.S. patent application Ser. No. 11/116,379, filed on Apr. 28, 2005, the disclosure of which is hereby incorporated herein by reference in its entirety.

FIELD OF THE INVENTION

The invention generally relates to a method and apparatus for implementing radio frequency identification techniques, and more specifically, to a method and apparatus for tracking, inspecting and verifying orthopedic and surgical instruments in order to assess the surgical instruments' duty life cycle usage.

DESCRIPTION OF RELATED ART

A variety of methods exist for tracking and providing information about items. For example, inventory items typically carry printed labels providing information such as serial numbers, price, weight, and size. Some labels include data carriers in the form of machine-readable symbols that can be selected from a variety of machine-readable symbologies, such as bar code or area code symbologies. The amount of information that the symbols can contain is limited by the space constraints of the label. Updating the information in these machine-readable symbols typically requires the printing of a new label to replace the old.

Tracking and managing orthopedic and surgical instruments used by hospitals is important to the efficiency and safety of use of large and specialized hand held orthopedic and surgical instruments, as well as for cost-related issues. Orthopedic and surgical instruments typically are manufactured from high-grade stainless steel that are designed to be used in cutting, clamping, retracting, chiseling, and fixating. Normally, orthopedic and surgical instruments are gathered after an operation or other procedure so that they can be sterilized. The recommended procedure for keeping the instruments in a working condition is to autoclave them by placing the instruments in a pressure vessel that first exhausts the air before releasing high-pressure (and therefore high-temperature) steam into the chamber that penetrates every part of the instrument. Another method of sterilizing the instruments is to chemically sterilize them by using ethylene oxide sterilization, which employs a process similar to the autoclaving cycle to ensure total penetration of all contours. Many plastic items and some types of rubber are damaged by repeated autoclaving, and prolonged immersion of the instruments in a sterilizing solution may damage the instruments.

Some of the existing methods of tracking and managing surgical instruments employ color-coding techniques to identify the different instruments. Others optically mark each instrument, and later scan the instruments with a hand-held scanner, such as, for example, a bar code scanner, that is connected to a data terminal to ascertain the identity and optionally the transactional history of that instrument. Such a method typically requires that the instrument be removed from the tray on arrival and individually scanned by an operator, a method that is costly, and time-consuming.

Bar code labels have received widespread use from product tracking in the package delivery business, to physical inventory tracking and even point-of-sale terminals. In some respects, due to their machine readable nature, bar code labels represent a significant improvement over printed labels. Also, they are relatively cheap and easy to generate with a printer. There are some limitations to bar codes, however, that limit their application to surgical instruments and trays. Bar codes are limited in size by resolution limitations of bar code scanners, and the amount of information that the symbols can contain is limited by the physical space constraints of the label. Therefore, some objects may be unable to accommodate bar code labels because of their size and physical configuration. In the field of surgical instruments, this may preclude bar code labels from some smaller or non-geometrically shaped instruments. In addition, labels only store a number that is meaningless until associated with a database.

Another limitation of bar code readers is that they require line of sight in order to read the reflection pattern from a bar code. One problem is that as labels become worn or damaged, and they can no longer be read with the bar code scanner. This is particularly likely in the field of surgical instrument trays because of the harsh conditions the labels must undergo during sterilization. Also, because a person operating the bar code scanner must physically orient either the scanner or the product to achieve line of sight on each item being scanned, items must be scanned one at a time resulting in prolonged scan time. In addition, because bar code scanning requires the operator to handle each instrument in order to scan it, a potential safety problem is created. Soiled instruments pose a biohazard because they may have come in contact with bodily fluids, and often have sharp edges. After the instruments have been sterilized, they should not be touched again until surgery to prevent contamination. Therefore, direct human contact either pre or post sterilization may be problematic. Another limitation of bar code labels is that they are static. Updating the information in these machine-readable symbols typically requires printing a new label to replace the old.

Data carriers such as memory devices provide an alternative method for tracking and providing information about items. These devices permit the linking of large amounts of data with an object or item. Memory devices typically include a digital memory, logic in the form of an integrated circuit ("IC") and a mechanism for transmitting data to and/or from the device. For example, a radio frequency identification ("RFID") tag typically includes a memory for storing data, an antenna, an RF transmitter, and/or an RF receiver to transmit data, and logic for controlling the various components of the memory device. The basic structure and operation of RFID tags can be found in, for example, U.S. Pat. Nos. 4,075,632, 4,360,801, 4,390,880, 4,739,328 and 5,030,807, the disclosures of which are incorporated herein by reference in their entirety. RFID tags are generally formed on a substrate and can include, for example, analog RF circuits, digital logic and memory circuits. RFID tags also can include a number of discrete components, such as capacitors, transistors, and diodes. The RF transmission of data can be accomplished with modulated back scatter as well as with modulation of an active RF transmitter.

RFID tags can either be passive or active devices. Active devices are self-powered, by a battery for example. Passive devices do not contain a discrete power source, but rather, derive their energy from an RF signal used to interrogate the RFID tag. Passive RFID tags usually include an analog circuit that detects and decodes the interrogating RF signal and that provides power from the RF field to a digital circuit in the tag. The digital circuit generally executes all of the data functions of the RFID tag, such as retrieving stored data from memory and causing the analog circuit to modulate to the RF signal to transmit the retrieved data. In addition to retrieving and transmitting data previously stored in the memory, the RFID tag can permit new or additional information to be stored in the RFID tag's memory, or can permit the RFID tag to manipulate data or perform some additional functions.

Another form of memory device is an optical tag. Optical tags are similar in many respects to RFID tags, but rely on an optical signal to transmit data to and/or from the tag. Additionally, touch memory devices are available as data carriers, (e.g., touch memory devices from Dallas Semiconductor of Dallas, Tex.). Touch memory devices also are similar to RF tags, but require physical contact with a probe to store and retrieve data.

It is desirable to be able to identify a suitable method of tracking orthopedic and surgical instruments to facilitate inventory operations and assist in performing repair and replacement of these instruments, should they become damaged or worn, that is not based solely on subjective visual inspection. However, devices attached to an orthopedic and surgical device or surgical instrument must be capable of performing despite being attached to various metals, and must be able to withstand the rigors of sterilization.

The description herein of various advantages and disadvantages associated with known apparatus, methods, and materials is not intended to limit the scope of the invention to their exclusion. Indeed, various embodiments of the invention may include one or more of the known apparatus, methods, and materials without suffering from their disadvantages.

SUMMARY OF THE INVENTION

Thus, there is a need to provide an inventory system for medical, orthopedic and surgical instruments that is more efficient for reducing handling costs, automating the verification process of items such as orthopedic and surgical instruments, and to overcome the aforementioned shortcomings of conventional identification techniques.

Embodiments of the invention provide systems and methods for automatically and wirelessly inventorying orthopedic and surgical instruments and the like, by retrieving information from the instrument and performing one or more operations on the data, such as, storing the data, comparing it against previously stored data, and/or recording new data. The information preferably may include information indicative of the manufacturer, part number, serial number and manufacturing data, usage and maintenance history of each instrument, and the like. The inventive systems and methods allow for lower handling costs of surgical instruments, increase the accuracy of the verification process of data pertaining to each instrument with a reduction of human contact, and provide for real-time data collection resulting in fast data acquisition that speeds up the inventory updating of such instruments.

Embodiments of the invention also are capable of circumventing some of the problems associated with manual removal and scanning of surgical instruments by implementing radio frequency tagging of each instrument, and creating a database on a wireless reader in order to wirelessly compare and ascertain the history of each tagged instrument as it arrives in a distribution center. An RFID system preferably includes three components: (i) an antenna or coil; (ii) a transmitter/receiver (transceiver) with a decoder; and (iii) an RF tag that is the transponder (tran(smitter)+(re)sponder) that is electronically programmed with certain unique information. The antenna emits radio frequency waves to activate the transponder (tag) in order to read or write data to it. In turn, the tag transmits data back to the antenna, and the data can be used to interface with a database to carry out a function such as inventory processing. One advantage of using RFID is that it does not require direct contact or line-of-sight scanning.

A feature of an embodiment of the invention provides a system and method for automatically and wirelessly inventorying orthopedic surgical instruments and the like. The system and method preferably retrieves information from an RFID transponder tag attached or integral to the orthopedic and surgical instrument, such as information that is indicative of the manufacturer, part number, serial number, manufacturing data, usage, and maintenance history, and maintenance scheduling of each instrument. The system and method allows for lower handling costs of orthopedic and surgical instruments, increases the accuracy of verification process of data pertaining to each instrument with a reduction of human contact, and provides real-time data collection resulting in fast data acquisition, which ultimately speeds up inventory updating of such instruments.

According to a feature of an embodiment of the invention, an instrument tray, having one or more orthopedic and surgical instruments positioned thereon is provided, each instrument comprising one or more radio frequency identification tags (RFID tags) that identify each instrument and the accompanying tray. It is preferred, though not required, that the tags identify each instrument in terms of manufacturer, part number, name, usage, and maintenance history. The method includes presenting a plurality of orthopedic and surgical instruments into a wireless radio frequency field of a reader device that emits an RF signal, activating all the RFID tags present, and enabling a response by the tags via a transceiver/antenna combination. The transceivers along with the antenna, collect data from the RFID tags and pass the data in a wireless fashion to the wireless reader to determine actions needed to be taken such as refurbishing, discarding or any other action(s) deemed necessary of the instruments.

Another embodiment of the invention provides a system and method for identifying and inventorying instruments used in orthopedic and surgical procedures. This embodiment provides a plurality of RFID tagged orthopedic and surgical instruments, wherein each RFID tag contains data identifying a corresponding instrument. In a preferred embodiment, orthopedic and surgical instruments are tagged with an RFID tag placed on a non-metallic part of the instrument, such as embedding the tag in a rubber handle, plastic surface, or other part of the instrument that may not interfere with the radio frequency signal. In response to an interrogation signal, the RFID tags on the instruments respond by transmitting a signal back to the transceiver/antenna combination, whereby the signal may contain data such as identification data. The data then is compared against data stored in a database containing information about the contents of each orthopedic and surgical instrument. Any messages resulting from this comparison may be displayed on a screen of the reader device.

In an embodiment of the present invention, individual orthopedic and surgical instruments are collected from warehouse racks, then RFID tags are placed on non-metallic parts of instruments, and placed back on the racks. In the event that one or more orders are received from one or more clients for one or more orthopedic and surgical instruments, the order is picked, and an RFID reader is brought in close proximity to the instrument RFID tags. The RFID reader may be a mobile stand-alone reader that can be wheeled into a collection area close to where the instruments are placed, or it may be fixed over a conveyor belt. In a preferred embodiment, the reader may be one of a group of consisting of: a desk-top PC, a personal digital assistant (PDA), a laptop PC, or a notebook PC, all of which are able to wirelessly transmit any data that is read into or collected from the RFID tags that are affixed to the orthopedic and surgical instruments, to the client.

Another embodiment of the present invention provides systems and methods for identifying medical and orthopedic and surgical instruments in an instrument tray, wherein outbound instrument trays are packaged together in a warehouse, and wherein inbound instrument trays that arrive from customers are received and processed. A typical system of this embodiment includes, but is not limited to, an instrument tray, desk-top personal computer(s), lap-top computer(s), personal digital assistant(s) (such as Palm™ Tungsten™), and/or sub-notebook. Various combinations of these items may be included in the system, and not all items need be present. These items comprise a wireless fidelity (WIFI) local Area Network that implements a peer-to-peer network, thereby allowing all the wireless equipment in the warehouse to communicate with each other without the need for a gateway or an access point.

One aspect of this embodiment provides a method whereby: (i) an instrument tray, together with a plurality of RFID tagged medical or orthopedic and surgical instruments, arrives at a central distribution center; (ii) a hand-held Wi-Fi-capable personal digital assistant transmits an interrogation signal; (iii) in response to the interrogation signal, a transceiver/antenna combination that is incorporated into the plurality of tagged instruments, including the instrument tray, interrogates the RFID tagged items and receives a data signal back; (iv) the plurality of tagged instruments transfers the data to the hand-held personal digital assistant; and (v) the data are compared to information maintained in a local database pertaining to the history of each individual instrument and tray.

Other aspects and advantages of the invention will become apparent from the following detailed description, taken in conjunction with the accompanying drawings, illustrating by way of example the principles of the invention.

BRIEF DESCRIPTION OF THE DRAWINGS

Purposes and advantages of the present invention will be apparent to those of ordinary skill in the art from the following detailed description in conjunction with the appended drawings in which like reference characters are used to indicate like elements, and in which.

DETAILED DESCRIPTION OF THE PREFERRED EMBODIMENTS

The following description is intended to convey a thorough understanding of the invention by providing specific embodiments and details involving automated identification and accounting of surgical instruments and instrument kits. It is understood, however, that the invention is not limited to these specific embodiments and details, which are exemplary only. It further is understood that one possessing ordinary skill in the art, in light of known systems and methods, would appreciate the use of the invention for its intended purposes and benefits in any number of alternative embodiments, depending upon specific design and other needs.

As used herein, the terms "surgical instrument" or simply "instrument" will refer to any type of standard surgical instrument, including scalpels, forceps, tweezers, clamps, spreaders, etc., as well as procedure and even discipline specific instrument such as, for example, orthopedic surgical equipment. The principles disclosed herein will apply equally to any type of portable surgical instruments and/or equipment.

As used herein, the terms "RFID reader device" or simply "reader device" will refer to any type of known or currently unavailable reader device capable of generating an RF field and receiving a data signal from one or more RFID transponder tags in response to the RF field, including, but not limited to hand held reading devices, integrated reader work tables, conveyor-based reader devices and desktop reader devices.

As used herein, the term "RFID" will refer to any type of radio frequency-based identification technology operating in any known or previously unused frequency range, wherein a passive or active tag emits a signal containing stored information in response to being placed within the influence of an RF field. "RFID transponder tag" or simply "RFID tag" as used herein will refer to any type of RF identification tag, including, but not limited to active tags, passive tags, and capacitively and inductively coupled tags.

As used herein, the term "potting" will refer to a process for integrating an RFID tag with an item to be identified in which a recess is carved, notched or etched into a portion of the item, an RFID transponder tag is placed in the recess, and a material is filled in the remainder of the recess to secure the tag and to reduce and/or eliminate the recess.

Figure 1:
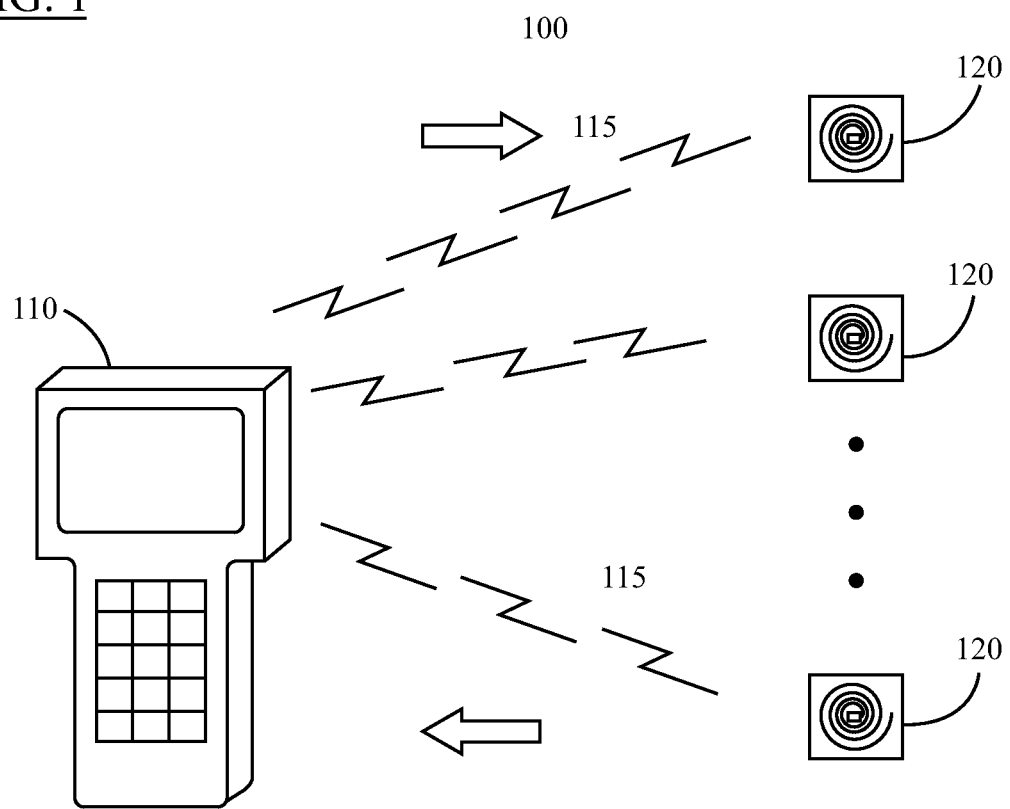
FIG. 1 illustrates a conventional radio frequency-based identification system for use with various embodiments of this invention.

Referring now to FIG. 1, a typical RF-based identification system 100 illustrated. The system shown in FIG. 1 comprises a reader device 110 and a plurality of RFID tags 120 which are usually attached or otherwise integrated into various products and other items to be identified. The reader device 110 shown in FIG. 1 is a hand held device, however, other types of reader devices, such as, for example, desktop reader devices, bench-type reading devices and other fixed reader devices, are known in the art. The reader device emits RF energy in the form of an RF field 115 that causes in the tags 120 to become energized and emit a signal containing information stored in their internal memory. The signal emitted by each of the various tags is captured by the reader device 110. As is often the case, either the reader device 110 contains an internal memory storing detailed information on the items to which the tags correspond, or the reader device 110 is in communication with a database located remote to the reader device 110, such as, for example, over a wired or wireless network. In this manner, information from the individual tags 120, such as an identification number, may be used to index a database which stores more detailed information on the item associated with the tag. Alternatively, if the tag, contains updatable memory, detailed information may be read directly from the tag and additional information may be written to the tags 120 with the reader device 110.

As discussed above, RFID tags are in widespread use in areas of inventory management and loss prevention. In these applications, the tags are formed on an adhesive-backed substrate that can be easily adhered to the various items to be inventoried. However, in these applications, the tags are essentially disposable—that is, once the products reach the consumer, the tag becomes useless. This is not the case with surgical instruments and other non-disposable equipment where the purpose of the tags is to be able to track and identify instruments and equipment throughout their life cycle. Moreover, as discussed herein, due to the harshness of the concomitant sterilization of surgical equipment, typical adhesion techniques will likely be insufficient to insure that the connection remains intact and the RFID transponder tag remains undamaged. Thus, as will be discussed in greater detail herein, other techniques such as embedding or potting the tags into a portion of the instrument to be identified may be utilized.

Figure 2:
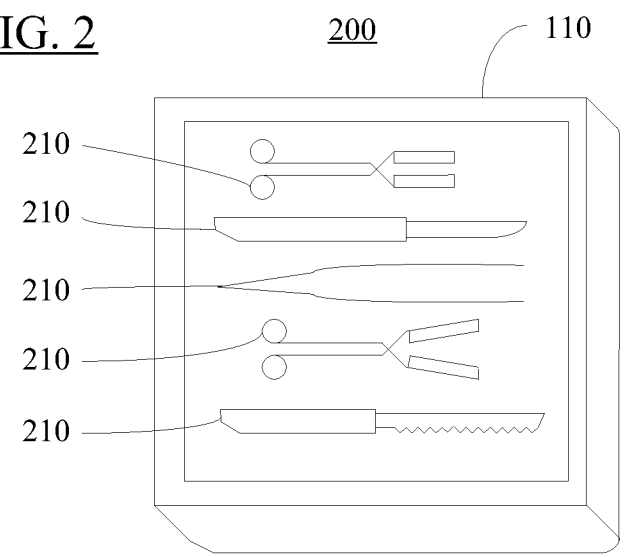
FIG. 2 is a perspective view of a conventional surgical instrument tray including a plurality of surgical instrument according to at least one embodiment of this invention.

Referring now to FIG. 2, a surgical instrument tray 200 having several surgical instruments 210 located thereon is illustrated. As shown in FIG. 2, the surgical instrument tray 210 comprises a box-like structure having a hollowed body and a roughly planar top surface surrounded on its perimeter by a raised lip that prevents instruments from sliding off of the tray. Typically, surgical instrument tray bodies are made of a plastic or other non-corrosive, relatively lightweight material such as titanium or stainless steel. In FIG. 2, for purposes of example only, the surgical instrument tray 210 is shown as being flat. However, it should be noted that surgical instrument trays may also contain one or more recesses shaped to receive various surgical instruments without departing from the spirit or scope of this invention. Alternatively, the surgical instrument tray may be of a kit configuration in which surgical instrument are placed inside the tray body in a drawer or box such that they can be enclosed by the tray body when direct access to the individual instruments is not required.

As noted herein, over time, and through ordinary usage, as well as due to the sterilization process, surgical instruments suffer wear and tear and eventually reach the end of their life cycle. Thus, it is necessary to periodically inspect and maintain records on the usage of surgical instruments so that they can be replaced as necessary. Also, due to the fact that they are constantly moved from the operating room to sterilization, to storage, and back to the operating room, various instruments on a given tray may become lost, or unrelated instruments from other trays may be added. Because certain instruments are so specialized that there are no functional substitutes, it has become necessary to regularly inspect trays for any missing instruments and to readily identify specific instruments that are missing or damaged. As discussed above, existing methods for performing these necessary functions are overly reliant on costly human interpretation. Also, in some cases, a skilled technician may be required to identify missing instruments. As with any human inspection process, the results are limited by the skill and accuracy of the person doing the inspecting.

By using RFID technology to identify surgical instruments in a batch mode, the instrument's identification number may be checked against stored information including usage records, date of first services, dates of sterilization, repair or other historical usage information. In various embodiments, a user will "read" an instrument using a hand held reader device. The read operation will cause the RFID transponder tag associated with the item to transmit a signal containing its stored information, either through information stored in a memory of the reading device or information stored in a database accessible by the reading device. The identification information will be used to retrieve a data record associated with that identification information. In various embodiments, this will cause the reader device to display a message on a screen integral to the device. In various embodiments the message may include information such as the actual name of the instrument, the date of manufacture of the instrument, the date of first use, dates of sterilization, and/or other relevant information. Also, the message may include any date triggered warnings. For example, if, based on the current date, it is determined that a scheduled service is recommended for the particular instrument, a message may appear on the screen either alone or in combination with an audible warning so that the user is prompted to set the particular instrument aside for scheduled service.

Figure 3:
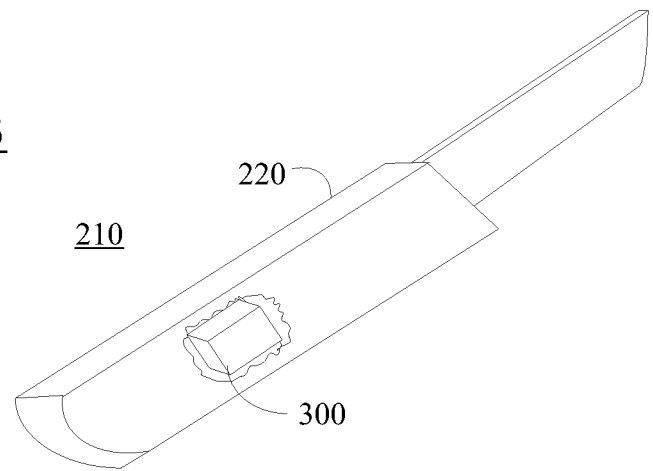
FIG. 3 is a cut away perspective view of a surgical instrument having an embedded RFID tag in a portion thereof according to at least one embodiment of this invention.

Referring now to FIG. 3, a surgical instrument 210 having an RFID transponder tag 300 embedded in a handle portion 220 thereof is illustrated in accordance with at least one embodiment of this invention. In the embodiment illustrated in FIG. 3, the tag 300 is embedded into the handle portion 220 of the instrument 210 at the time of manufacture and then seamlessly enclosed inside by the handle material. Embedding the tag overcomes problems associated with sterilization because the tag 300 is protected from liquid sterilants by the material surrounding it. However, in such embodiments, it is important that at least the portions of the instrument 210 surrounding the tag 300 are not made of metal or other conductive material. Using radio frequency tags with metallic objects such as stainless steel objects can present certain signal loss problems. These problems may be particularly acute for surgical instruments due to their high metal content. The metal used to fabricate the items may interfere with the transmission and reception of the radio frequency signals. Thus, while embedding does insure that the tag and object do not become separated and that the tag remains protected during sterilization, it is relatively expensive to implement because of the added complexity to the manufacturing process and the limits it puts on choice of materials.

Figure 4:
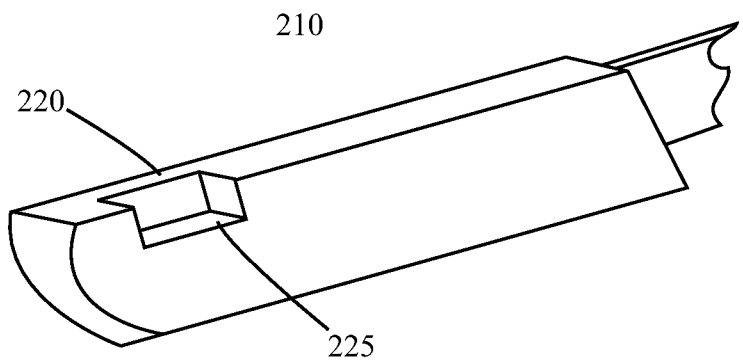
FIGS. 4-6 illustrates various stages of a process for potting an RFID tag in a portion of a surgical instrument according to at least one embodiment of this invention.
Figure 5:
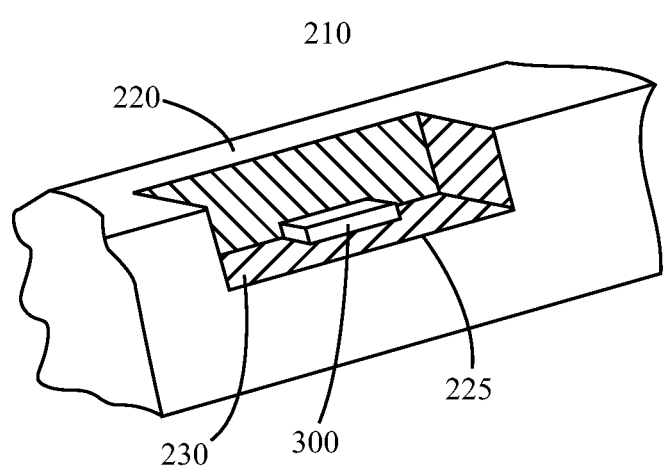
Figure 6:
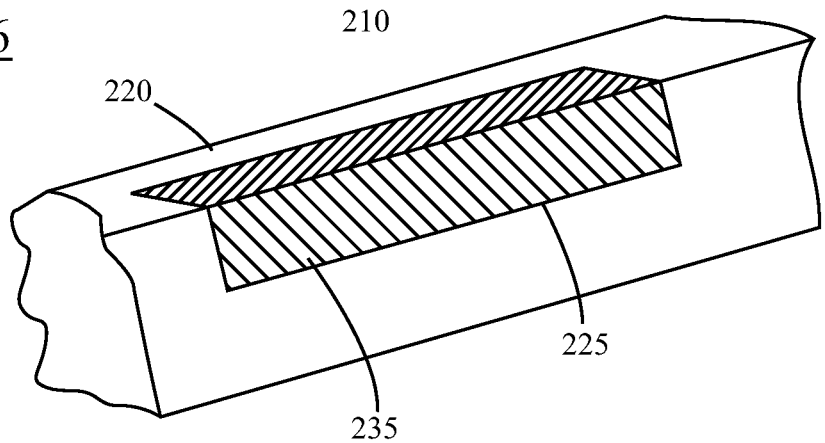
Figure 7:
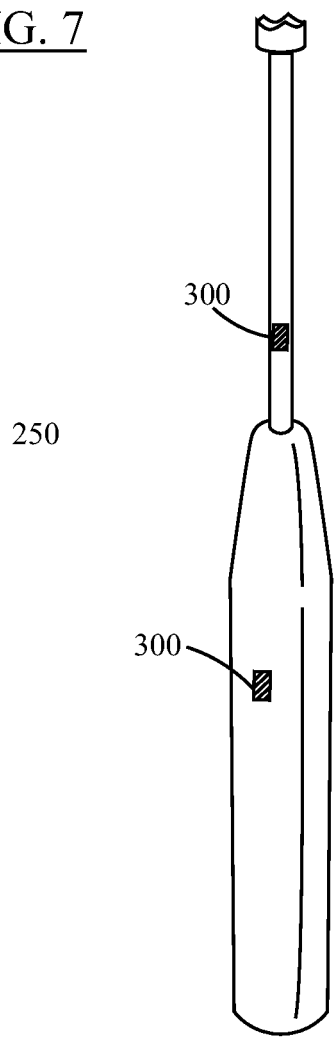
FIGS. 7-13 illustrate various orthopedic surgical instruments with RFID tags in accordance with at least one embodiment of this invention.
Figure 8:
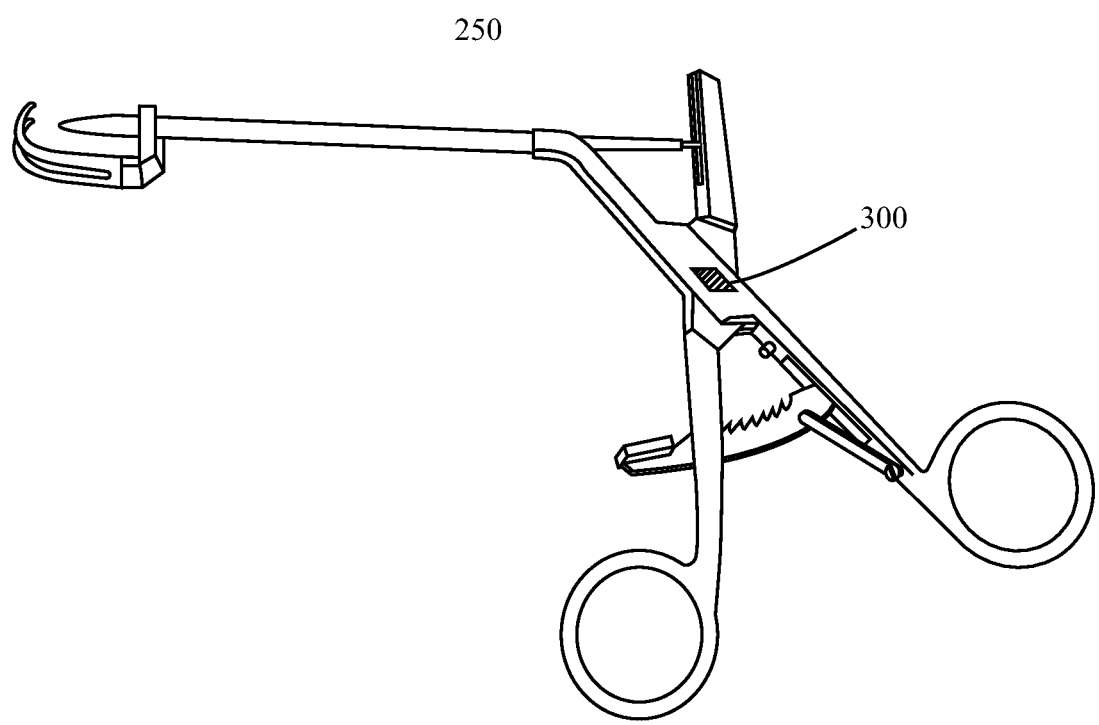
Figure 9:
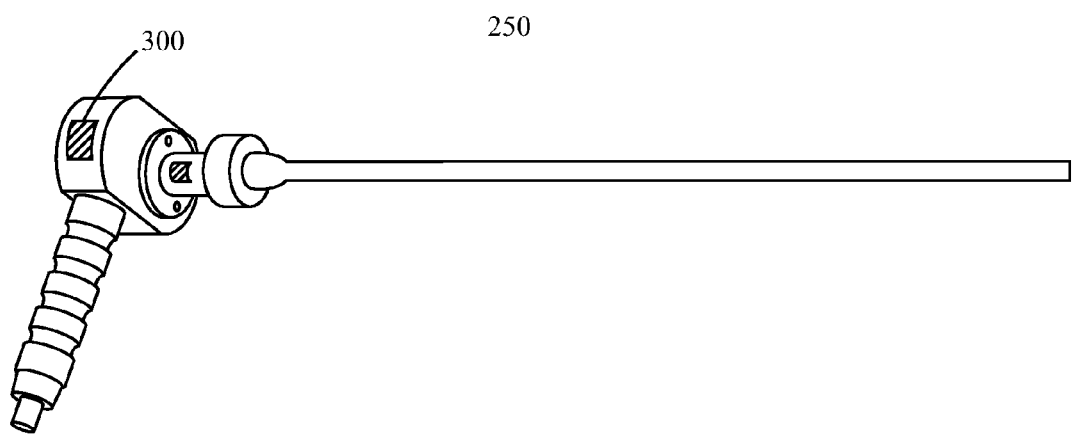
Figure 10:
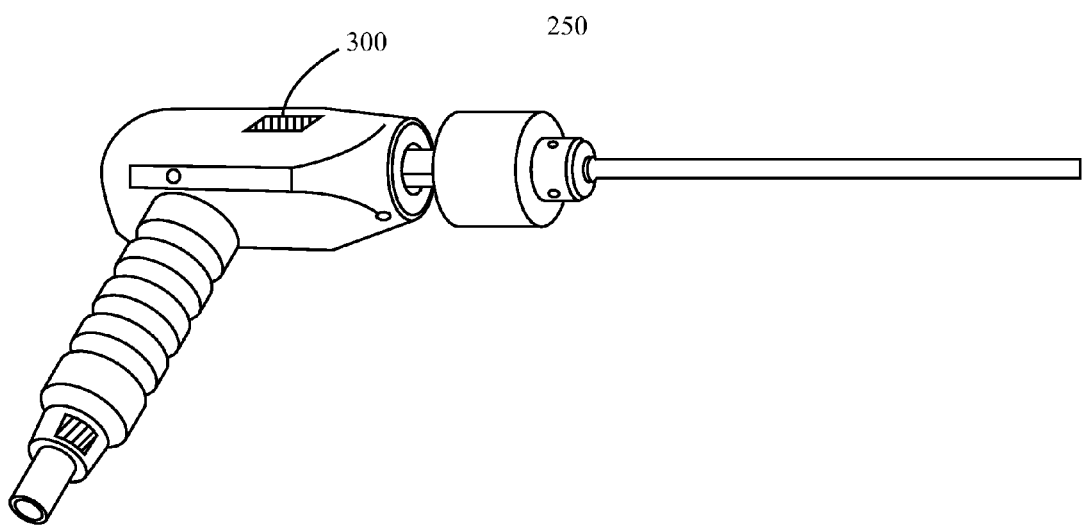
Figure 11:
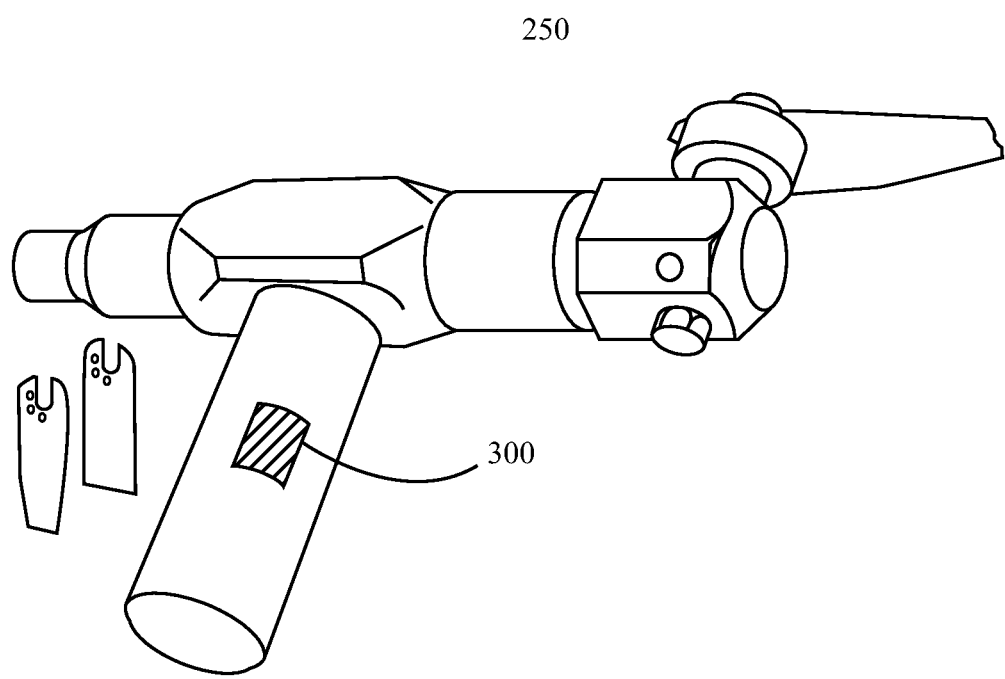
Figure 12:
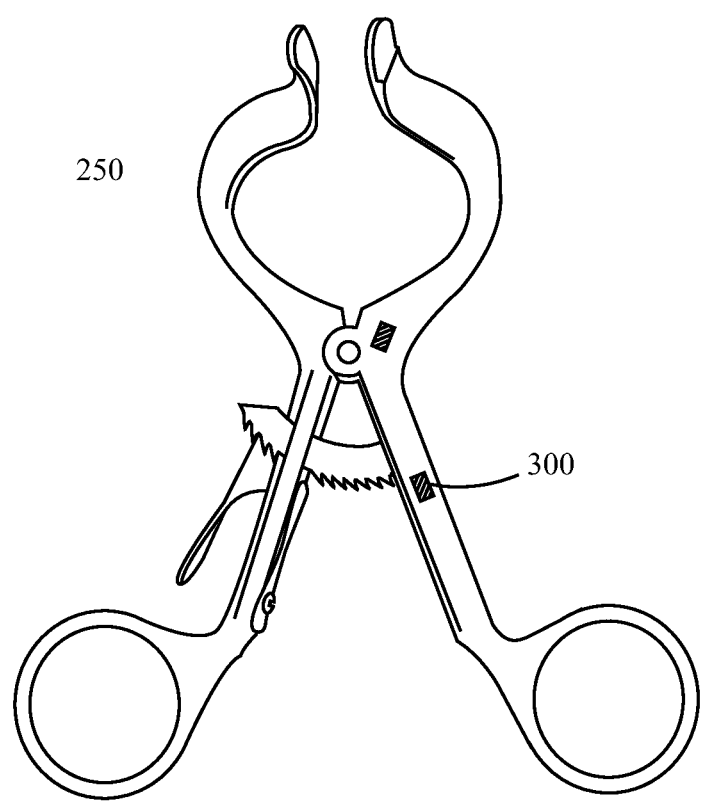
Figure 13:
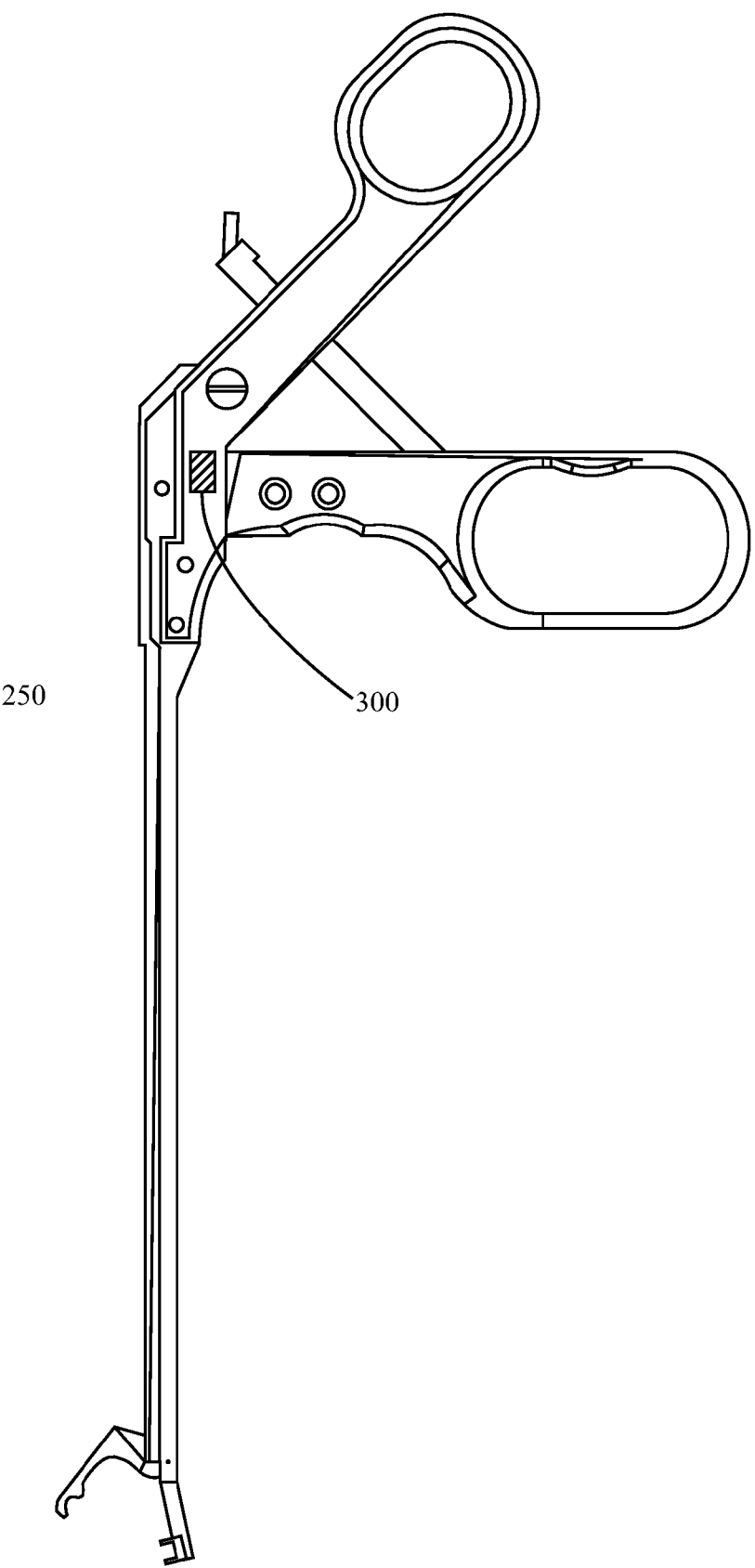

In view of the realities associated with embedding, an alternative attachment method is potting the tag in a portion of the item to be identified. Referring now to FIGS. 4-6, various steps of a process for potting an RFID transponder tag in a portion of a surgical instrument are illustrated. Taking a conventional surgical instrument 210, such as the scalpel shown in these Figures, a notch 225 is etched, ground or otherwise formed in the handle 220 of the instrument 210. While the notch 225 in these Figures is shown as encompassing a corner of the handle portion 220, it should be appreciated that it may alternatively be located in a face or in an end portion of the handle portion 220. The precise location of the notch 225 is not critical to the embodiments of the invention. In fact, notch 225 need not even be in the handle 220, but may be located in any other portion of the instrument having sufficient thickness that a notch may be cut without compromising the structural integrity of the instrument.

Once the notch 225 is formed, a preferably non-conductive material layer 230 can be formed in the notch to provide an insulating layer between the electrical components of the RFID transponder circuit and the potentially conductive material of the handle portion 220. By using this non-conductive material layer 230, metal, titanium and other strong but conductive materials may be used to form the surgical instrument 210 without compromising the effectiveness of the RFID tag.

Once the non-conductive material layer 230 has been formed, the tag 300 preferably is then affixed with an adhesive or other suitable affixation means to the handle portion 220. Next, a filling material 235 preferably is used to fill in the remainder of the notch 225, thus, eliminating the notch from the surface of the handle portion 220. The filling material 235 preferably will create a flush look to the handle portion 225 so that the RFID tag 300 is concealed behind the perceptible change in material but is otherwise unobtrusive. Alternatively, the filling material 235 may be blended in with the material used to form the handle portion 220, thereby resulting in a littler or no perceived change in material. In various embodiments, the filling material 235 will be comprised of a non-conductive material through which RF waves may easily pass without attenuation. For example, in various embodiments, the filling material 235 will be a material such as Phenol, Glass, Wood, Epoxy resin, Silicon, Rubber, Polyvinyl Chloride, commonly known as PVC, Acrylonitrile Butadiene Styrene, known as ABS resin, common plastics, Styrofoam, etc., but may include other suitable materials. It also is understood by skilled artisans that an air-gap may be required between the RFID tag, and the tagged instrument on one hand, and between the RFID tag and its encasement. Using the guidelines provided herein, those skilled in the art will be capable of designing a suitable RFID tag to be used on an instrument tray and/or a variety of orthopedic and surgical instruments.

Referring now to FIGS. 7-13, various orthopedic surgical instruments having one or more RFID tags are illustrated in accordance with various embodiments of the invention. Specifically, a crown fixator, a vogen sesamoid clamp, a reaming hand piece, a drilling handpiece, a saggital saw, a cox metatarsal spreader and a set of forceps are illustrated. Each of the orthopedic surgical instruments 250 comprises a one or more RFID tags 300 that are integrated with the instruments 250 using one or more of the methods discussed herein, such as, for example, by adhesion, embedding and/or potting. Though not necessary, in a preferred embodiment, the tags 300 are located on these items at locations designed to minimize and ideally eliminate any obtrusion to the person using the equipment and/or the person, animal or thing the instrument is used on. The externally mounted appearance of the tags 300 is for ease of illustration only. The tag actually may be embedded or potted in the instrument at the location indicated in the Figures. Furthermore, by having the integral RFID tags, these items may be identified in bulk, may be discovered in trash, and may be discovered if accidentally left in the body cavity of a patient and without physical contact, subjective interpretation and/or visual inspection. Moreover, detailed records may be maintained on the instruments without requiring highly trained personnel to identify all the different types of instruments.

While the foregoing description includes many details and specificities, it is to be understood that these have been included for purposes of explanation only, and are not to be interpreted as limitations of the present invention. Many modifications to the embodiments described above can be made without departing from the spirit and scope of the invention.

What is claimed:

1. A system for determining if an action needs to be taken upon the contents of a surgical instrument tray, comprising:
   a surgical instrument tray having at least one surgical instrument comprising an RFID transponder tag embedded in a portion of the at least one surgical instrument and having identification information corresponding to the at least one surgical instrument stored in a memory therein, the at least one surgical instrument including a handle portion comprising a conductive material, the tag being enclosed in the handle portion by a non-conductive material such that the non-conductive material is continuous with an outer surface of the handle portion; and
   a reader device that, when placed in proximity to the at least one instrument, generates an RF field of sufficient strength to cause the RFID transponder tag to emit a signal containing at least some of its stored identification information, the signal being received by the reader device; and a database coupled to the reader device for storing information corresponding to the identification information read by the reader device.

2. The system of claim 1, wherein the tag is seamlessly enclosed in the handle portion of the surgical instrument using the non-conductive material.

3. The system of claim 2, wherein the tag is enclosed in the handle portion using a silicone overmolding.

4. The system of claim 1, wherein the identification information comprises information selected from the group consisting of a number of times that servicing has been performed on the instrument and a set of dates that servicing has been performed on the instrument.

5. The system of claim 4, wherein servicing includes autoclaving or ultrasonic cleaning.

6. The system of claim 1, wherein the reader device retrieves a data record from the database based on the received identification information and determines if any additional surgical instruments are missing from the surgical instrument tray and if any of the at least one surgical instrument is improperly located in the surgical instrument tray based, at least in part, on the data record and the identification information.

7. The system of claim 1, wherein the at least one surgical instrument includes an insulating layer between the tag and the handle portion of the surgical instrument.

8. The system of claim 7, wherein the tag is formed on an adhesive-backed substrate, the substrate being adhered to the insulating layer.

9. The system of claim 7, wherein the non-conductive material comprises phenol, glass, wood, epoxy resin, silicon, rubber, polyvinyl chloride, acrylonitrile butadiene styrene, plastics, or styrofoam.

10. The system of claim 7, wherein the non-conductive material is blended with the conductive material such that there is little or no perceived change in material.

11. The system of claim 7, wherein the insulating layer and the tag are disposed in a notch extending into the outer surface of the handle portion.

12. The system of claim 1, wherein an air-gap is present between the handle portion and the tag.

13. The system of claim 1, wherein an air-gap is present between the tag and the non-conductive material.

* * * * *